United States Patent
Charlot et al.

(10) Patent No.: US 10,885,148 B2
(45) Date of Patent: Jan. 5, 2021

(54) SYSTEM AND METHOD FOR MEDICAL CLASSIFICATION CODE MODELING

(71) Applicant: Intelligent Medical Objects, Inc., Northbrook, IL (US)

(72) Inventors: Regis Charlot, Lake Bluff, IL (US); Frank Naeymi-Rad, Libertyville, IL (US); Michael Decaro, Mount Prospect, IL (US); Steven Rube, Lake Forest, IL (US); Eric Rose, Seattle, WA (US); Andrew Kanter, Highland Park, IL (US); David Parks, Barrington, IL (US); Daniel Emmons, Highwood, IL (US); Alina Oganesova, Highland Park, IL (US); David Alvin, Glen Ellyn, IL (US); Matthew Cardwell, Oak Park, IL (US)

(73) Assignee: INTELLIGENT MEDICAL OBJECTS, INC., Rosemont, IL (US)

( * ) Notice: Subject to any disclaimer, the term of this patent is extended or adjusted under 35 U.S.C. 154(b) by 1148 days.

(21) Appl. No.: 14/817,912

(22) Filed: Aug. 4, 2015

(65) Prior Publication Data
US 2016/0283673 A1    Sep. 29, 2016

Related U.S. Application Data

(60) Provisional application No. 62/137,374, filed on Mar. 24, 2015.

(51) Int. Cl.
*G06F 19/00* (2018.01)
*G06F 16/248* (2019.01)
(Continued)

(52) U.S. Cl.
CPC .......... *G06F 19/32* (2013.01); *G06F 16/248* (2019.01); *G06F 16/24573* (2019.01); *G06F 16/972* (2019.01); *G16H 40/20* (2018.01)

(58) Field of Classification Search
None
See application file for complete search history.

(56) References Cited

U.S. PATENT DOCUMENTS

| | | |
|---|---|---|
| 5,799,268 A | 8/1998 | Boguraev |
| 5,930,788 A | 7/1999 | Wical |

(Continued)

OTHER PUBLICATIONS

"Semantic Web: Asking the Right Questions," Duch et al., Seventh International Conference on Information and Management Sciences, Urumchi, China, Aug. 12-19, 2008 entire document www.fizyka.umk.pl/ftp/pub/papers/kmk/08-SemWeb.pdf.

(Continued)

*Primary Examiner* — Michael Tomaszewski
*Assistant Examiner* — Jay M. Patel
(74) *Attorney, Agent, or Firm* — Quarles & Brady LLP

(57) ABSTRACT

A medical classification code modeling system and method that generates visual maps in response to user queries, where the visual maps represent combinations of modifiers of an interface terminology that, taken together, map to medical classification code elements. The system and method may present multiple visual maps on the same display to permit visual analysis of multiple mapping revisions or versions. The system and method further may integrate into an electronic health record such that the user's ultimate selection of a mapping results in the corresponding medical classification code being inserted into the record of a patient at an appropriate location, such as on the patient's problem list.

20 Claims, 14 Drawing Sheets

(51) Int. Cl.
  *G06F 16/2457* (2019.01)
  *G16H 40/20* (2018.01)
  *G06F 16/958* (2019.01)

(56) References Cited

U.S. PATENT DOCUMENTS

| | | | |
|---|---|---|---|
| 6,055,540 A | 4/2000 | Snow et al. | |
| 6,101,515 A | 8/2000 | Wical et al. | |
| 6,904,432 B2 | 6/2005 | Charlot et al. | |
| 7,167,858 B2 | 1/2007 | Naeymi-Rad et al. | |
| 7,496,593 B2 | 2/2009 | Gardner et al. | |
| 7,536,387 B2 | 5/2009 | Charlot et al. | |
| 7,693,917 B2 | 4/2010 | Charlot et al. | |
| 7,711,671 B2 | 5/2010 | Meyers | |
| 7,870,117 B1 | 1/2011 | Rennison | |
| 8,346,804 B2 | 1/2013 | Phillips | |
| 2002/0128861 A1 | 9/2002 | Lau et al. | |
| 2003/0179228 A1 | 9/2003 | Schreiber et al. | |
| 2005/0149510 A1* | 7/2005 | Shafrir | G06F 16/3338 |
| 2005/0240572 A1 | 10/2005 | Sung et al. | |
| 2006/0069677 A1 | 3/2006 | Tanigawa et al. | |
| 2007/0179776 A1 | 8/2007 | Segond et al. | |
| 2008/0065452 A1 | 3/2008 | Naeymi-Rad et al. | |
| 2008/0104032 A1 | 5/2008 | Sarkar | |
| 2008/0154873 A1* | 6/2008 | Redlich | G06F 16/2425 |
| 2008/0306926 A1 | 12/2008 | Friedlander et al. | |
| 2009/0070103 A1* | 3/2009 | Beggelman | G06F 40/20 704/9 |
| 2009/0083231 A1 | 3/2009 | Eberholst et al. | |
| 2009/0254572 A1 | 10/2009 | Redlich et al. | |
| 2010/0063799 A1* | 3/2010 | Jamieson | G06F 16/36 704/9 |
| 2010/0094649 A1* | 4/2010 | White | G06Q 50/22 705/2 |
| 2010/0169299 A1 | 7/2010 | Pollara | |
| 2010/0262659 A1 | 10/2010 | Christiansen et al. | |
| 2011/0066425 A1 | 3/2011 | Hudgins et al. | |
| 2011/0138050 A1 | 6/2011 | Dawson et al. | |
| 2011/0184960 A1 | 7/2011 | Delpha et al. | |
| 2011/0288877 A1* | 11/2011 | Ofek | G16H 10/60 705/2 |
| 2012/0110016 A1* | 5/2012 | Phillips | G06Q 50/22 707/780 |
| 2012/0179696 A1 | 7/2012 | Charlot et al. | |
| 2012/0215560 A1* | 8/2012 | Ofek | G16H 40/67 705/3 |
| 2013/0297328 A1* | 11/2013 | Johnson | G06F 19/00 705/2 |
| 2014/0122117 A1* | 5/2014 | Masarie, Jr. | G16H 10/60 705/3 |
| 2014/0350954 A1* | 11/2014 | Ellis | G16H 50/20 705/2 |
| 2014/0372148 A1* | 12/2014 | Reddy | G16H 40/20 705/3 |
| 2015/0066524 A1 | 3/2015 | Fairbrothers et al. | |
| 2015/0066539 A1* | 3/2015 | Sheffer | G16H 50/20 705/3 |
| 2015/0066974 A1* | 3/2015 | Winn | G16H 70/60 707/766 |
| 2015/0088548 A1* | 3/2015 | Charlot | G16H 10/60 705/3 |
| 2015/0095016 A1* | 4/2015 | Karres | G16H 10/20 704/9 |
| 2015/0213094 A1 | 7/2015 | Lou et al. | |
| 2015/0356246 A1* | 12/2015 | D'Souza | G06Q 30/0283 705/3 |
| 2015/0356260 A1* | 12/2015 | D'Souza | G06F 19/328 705/2 |
| 2015/0356646 A1* | 12/2015 | Spitznagel | G06F 19/328 705/2 |
| 2015/0356647 A1* | 12/2015 | Reiser | G16H 10/60 705/3 |
| 2016/0125024 A1* | 5/2016 | Blanco | G06Q 40/08 707/772 |
| 2016/0125025 A1* | 5/2016 | Blanco | G06F 16/2457 707/772 |

OTHER PUBLICATIONS

Virginia Tech SNOMED Core Structures 2nd AAHA Software Vendors Summit, Apr. 21, 2009.
"Social tagging overview (SharePoint Server 2010)" May 12, 2010 entire document http://technet.microsoft.com/en-us/library/ff608137.aspx.
Bronnert et al., Problem-Centered Care Delivery, Journal of AHIMA 83, No. 7 (Jul. 2012): 30-35.
Non-Final Office Action, related U.S. Appl. No. 15/078,806, dated Dec. 19, 2018, 29 pages.

* cited by examiner

SYSTEM AND METHOD FOR MEDICAL CLASSIFICATION CODE MODELING

This application claims the benefit of priority from U.S. provisional application 62/137,374, filed Mar. 24, 2015.

BACKGROUND

1. Field of the Invention

The present application is direct to a method and system for modeling medical classification codes.

2. Description of the Related Art

Medical classification code sets are used in multiple aspects of health care, e.g., in order to document patient encounters, generate complete electronic medical or health records, ensure complete, accurate billing, etc. One example of a medical classification code set is the World Health Organization's International Statistical Classification of Diseases and Related Health Problems, or "ICD."

Various modifications to the ICD classification system may exist depending on the country in which the codes are being applied. For example, the ICD code set in Australia is designated "AM," which represents the Australian Modification.

Alternatively, modifications may exist depending on the purpose behind the code set. Thus, in the United States, ICD-10-CM ("Clinical Modification") is a code set used for diagnosis and procedure coding, and ICD-10-PCS is used to code inpatient procedures.

Classification code sets are updated periodically, e.g., by adding new codes, deleting old codes, or modifying existing codes. Sometimes the updates are relatively minor, and sometimes the updates reflect significant changes in the code model. For example, in the United States, ICD-CM is transitioning from the 9th to the 10th revisions, i.e., from ICD-9-CM to ICD-10-CM. ICD-9-CM includes approximately 13,000 distinct codes, whereas ICD-10-CM currently includes roughly 68,000 codes. Many of the updates reflect a desire to capture a greater amount of information in a single code, e.g., including laterality (left/right/unspecified/ etc.) or creating codes that reflect both symptoms and a diagnosis.

In order to operate efficiently, a health care computer system may incorporate these changes to provide end users with the benefits of the greater granularity that the new code set provides. At the same time, it may be beneficial for the updates to occur in a back-end environment, in order to minimize an impact on end user workflow.

In addition to the difficulties that may result from the differences between code sets or release versions of a single code set, an end user may face difficulties in selecting the appropriate classification code due to the sheer number of possible codes that are available. For example, a root term like "diabetes" may yield more than 600 variants in the ICD-10-CM system.

Thus, when migrating between releases of classification code sets, it can be tedious to determine if the mappings are correct, or if all possible mappings are accounted for. Additionally, when searching for a desired variant within a code set, it may be difficult for the user to find that desired variant when presented with dozens, if not hundreds, of options. Moreover, users may be required to select the most specific classification code and may have to explore multiple variant combinations before locating the combination that maps to that classification code.

One system and method for seeking out a desired code is disclosed and claimed in the commonly-owned U.S. patent application Ser. No. 14/598,076, filed Jan. 15, 2015, the contents of which are incorporated by reference in their entirety. In that case, a computer system may receive a search request from a user and prompt the user to provide additional information in the form of one or more variants, which may include at least one of a clinical modifier, a non-clinical modifier, a laterality, and a status modifier. Upon receiving the selected variant(s), the system may determine which of the codes in the set matches the selected criteria and present those results to the user, either for additional specification or to receive a user selection of a more specific interface term, leading to an appropriately-specific classification code.

While this method may be effective in getting a user to the desired end result, other methods also may be beneficial.

BRIEF SUMMARY

In one aspect, a method for medical classification code modeling includes the steps of: mapping, using a computer, a plurality of medical classification codes to a plurality of interface plurality terminology elements, grouping the plurality of interface terminology elements into categories in a database, each category comprising a base element and one or more sub-elements, where each sub-element is represented as a combination of the base element with one or more modifiers selected from among one or more variants, receiving, using a computer, a search query from a user, comparing the search query against the database, determining, by the computer, whether the search query matches one or more base elements, returning a list of base elements matching the search query matches, receiving a user selection of one of the search query matches, and generating a visual map of the one or more sub-elements underneath the user selection. The generating step may include arranging modifiers according to their respective variants and visually linking the one or more modifiers that represent each sub-element. In addition, the combinations may be generated automatically or, alternatively, may be created by a human terminology upon making a clinical determination.

In another aspect, a method for medical classification code modeling includes the steps of: mapping, using a computer, a plurality of medical classification codes to a plurality of interface plurality terminology elements, grouping the plurality of interface terminology elements into categories in a database, each category comprising a base element and one or more sub-elements, where each sub-element is represented as a combination of the base element with one or more modifiers selected from among one or more variants, receiving a search query from a user on a second computer, comparing the search query against the database, determining, by the computer, whether the search query matches one or more base elements, and returning, to the second computer, a data file including a list of base elements matching the search query matches. The data file may include data and instructions to generate a visual map of the one or more sub-elements underneath a user selection of one of the search query matches. The instructions also may include arranging modifiers according to their respective variants and visually linking the one or more modifiers that represent each sub-element.

In still another aspect, a system for medical classification code modeling may include: a first computer system having a processor and at least one database, the first computer system in communication via a web service with one or more user computers, the at least one database including data representing a mapping of a plurality of medical classification codes to a plurality of interface plurality terminology elements. The at least one database may group the plurality of interface terminology elements into categories, each category including a base element and one or more sub-elements, where each sub-element includes a combination of the base element with one or more modifiers selected from among one or more variants. The first computer system also may be configured to compare a search query received from a second computer against the database and to determine whether the search query matches one or more base elements. Moreover, the first computer system may be configured to generate and to transmit to a second computer system a data file including a list of base elements matching the search query matches. The data file may include data and instructions to generate a visual map of the one or more sub-elements underneath a user selection of one of the search query matches, and the instructions may include arranging modifiers according to their respective variants and visually linking the one or more modifiers that represent each sub-element.

The method, and the system for carrying out the method, may generate a single visual map that may be particularly well-suited to assisting a user in finding a desired more specific clinical interface term leading to, i.e., mapping to a medical classification code.

Additionally or alternatively, the method and system for carrying out the method may generate multiple visual maps that may be particularly well-suited to comparing versions or revisions of mappings, e.g., for quality assurance or other purposes.

DETAILED DESCRIPTION

Figure 1:
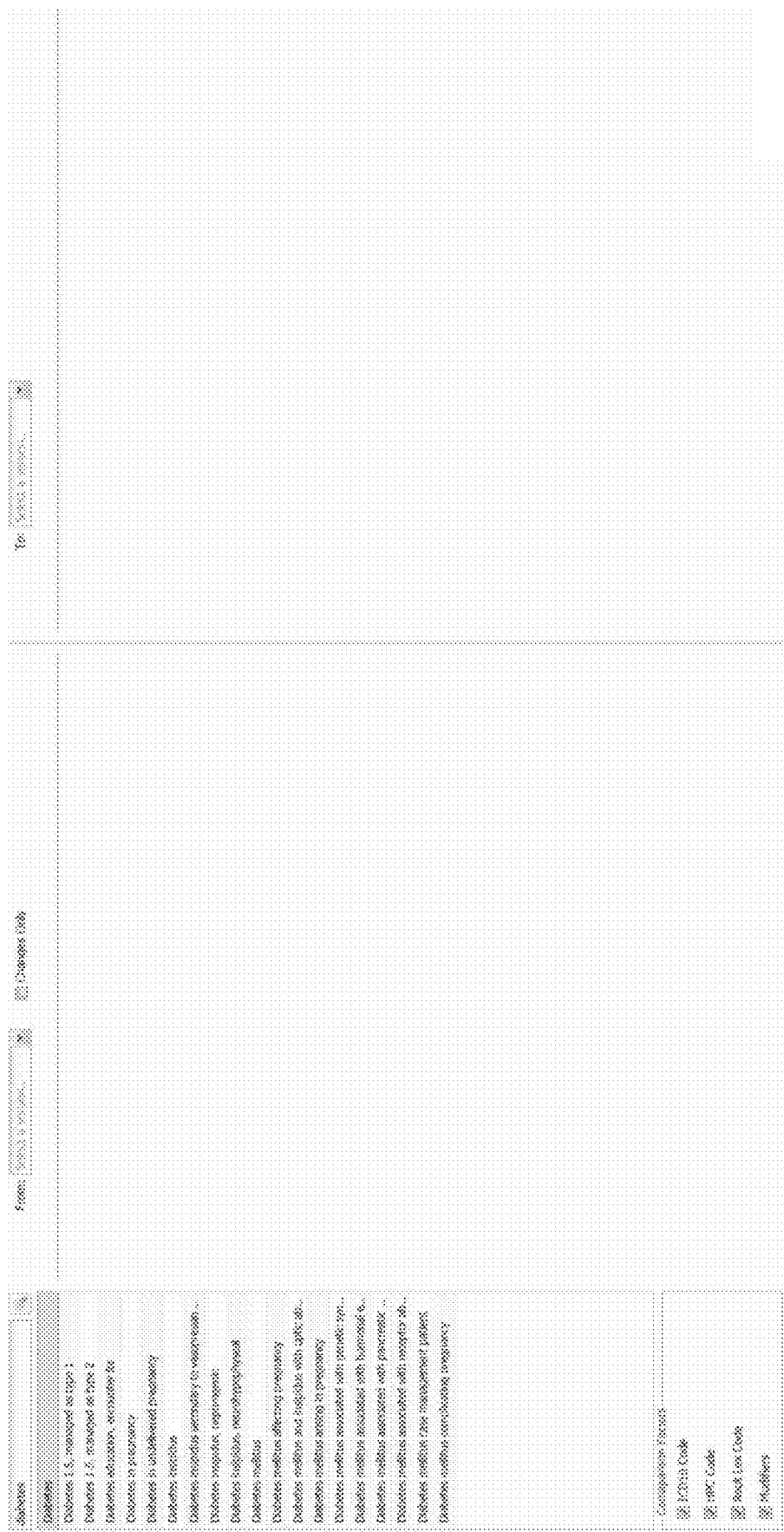
FIG. 1 is a screenshot of a user interface configured to receive a user query for a medical classification code, to return potential search results, and to generate and display visual maps to a plurality of interface terminology or medical classification code elements within a plurality of versions, revisions, etc., of those codes.

The present system and method for medical classification code modeling provide a top-down or global view to determine a desired medical classification code and/or to analyze the mappings between interface terminology elements and multiple classification codes, as opposed to other systems that may employ a bottom-up or constructive process. The mapping between the medical classification codes and interface terminology elements may be accomplished by mapping each medical classification code to a root interface terminology element and one or more interface terminology modifier elements.

Put another way, when a user is attempting to locate a desired classification code, it previously may have been difficult to visualize what effect, if any, different filter selections have on the workflow. It further may have been difficult to determine how accurate or complete a mapping scheme was or to understand how multiple classification codes relate to one another. The present system and method therefore provide a fast, intuitive depiction of mappings in order to assess completeness and accuracy of mappings from a development standpoint for modelers, as well as fast recognition and selection from an end-user implementation standpoint, e.g., for entering data to provide mappings for an electronic health record, either at the time of a patient encounter or at a later time by a user documenting the encounter. In one aspect, the depiction includes the grouping and display of elements of an interface terminology, where the elements include expressions of clinical intent.

Additionally, when a user seeks to compare one version of a mapping against another version, it may be difficult and time consuming to determine whether the more recent mapping is complete or otherwise correct. The present system and method therefore include a visual layer to present this information in an efficient, easy to understand way that permits rapid interaction and analysis of the mapping data. Additionally, the system and method may be configured so as to permit easy interaction with one or more additional software platforms, e.g., an electronic medical record software system that includes or interfaces with the system and method described herein.

As described in greater detail below, one manner in which the system and method accomplish these tasks is by generating an interactive visual mapping of components of an interface terminology that map all medical classification codes suggested as a result of the initial user query. The system then may receive user selections of one or more modifiers, where the system may remove visual representations of medical classification codes that do not include mappings to the selected modifiers.

One method of mapping user queries to returnable results may include building an interface terminology comprising a plurality of concepts within one or more domains and linking one or more descriptions to each concept, where each description reflects an alternative way to express the concept. Search results may include interface terminology descriptions or concepts. Aspects of this mapping may be found in one or both of the commonly owned U.S. patent application Ser. No. 13/004,128, filed Jan. 11, 2011, and U.S. patent application Ser. No. 13/660,512, filed Oct. 25, 2012, the contents of both of which are incorporated by reference in their entirety. Alternatively, the interface terminology may map to the medical classification code being modeled, and the search may occur using the interface terminology descriptions, whereas the returned results may be elements or sub-elements of the medical classification code.

In another alternative, the medical classification code being searched may be stored as a plurality of entries in a database, and the system may search the text of the database directly to return results that match elements within that database.

Depending on the degree of specificity provided by the user in the search, the search results may direct the user directly to the desired medical classification code. More often, however, the user may input enough information to narrow the possibilities down from several thousand to a handful or a few dozen.

The system and method may be used to compare or reconcile a plurality of medical classification code sets, which may be multiple, different code sets, or which may be different releases, revisions, or other variations of the same code set. Alternatively, the system and method may be used to compare or reconcile a plurality of interface terminology code sets to a medical classification code set, where the interface terminology code sets may be different code sets or different releases, revisions, or other variations of the same code set.

As described in greater detail below, each classification code entry may be mapped to a root interface terminology concept and/or to one or more root interface terminology descriptions, in addition to being mapped to one or more interface terminology modifier concepts and/or descriptions. Multiple modifiers may be grouped together in groups called variants. While a medical classification code may map to multiple modifiers, preferably it only maps to a single modifier per variant.

As seen in FIG. 1, a search function receives a user query and returns one or more results that include the search terms that match either exactly or approximately, e.g., within a predetermined confidence range. Each result may be either a fully-defined classification code concept or an interface terminology concept that maps to a classification code concept. More likely, results may be less than fully defined, such that even greater specificity is possible and, in fact, may be necessary in order to obtain a fully defined concept and its corresponding classification code value. These search results may be termed "root lexicals," and the additional specificity may be achieved through the use of one or more modifiers selected from among one or more variants.

Either before or after the system receives the search request and returns its results, the user may select the classification code sets, interface terminology release versions, etc., to compare. For example, the system may present a side-by-side series of windows proximate the search results with a drop-down-type menu associated with each window from which the user may select the desired code set. While the code sets being compared often may be consecutive releases, comparisons between non-consecutive revisions also may be permitted. For example, FIG. 2 shows a comparison between revisions 1.1 and 1.3 of a code set.

Figure 2:
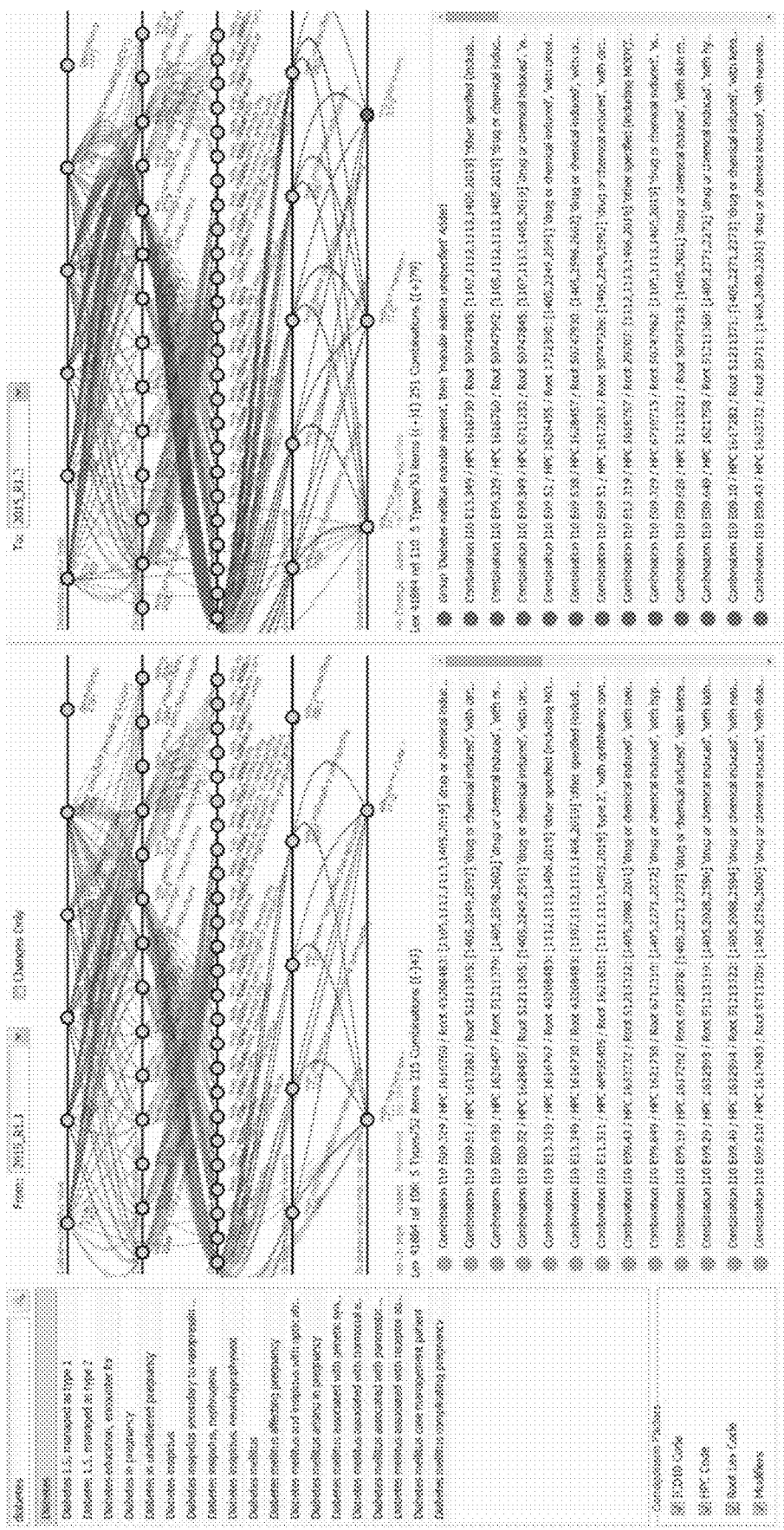
FIG. 2 is a screenshot of the interface of FIG. 1, displaying a plurality of visual maps and textual depictions on the same display, each visual map including a plurality of splines reflecting relationships between multiple code variants and modifiers within those variants.

Staying with FIG. 2, after receiving the user's search request and presenting the user with one or more possible root lexical results, the system may receive a selection from the user of an entry within the results list. Upon receiving the selection and highlighting that selection for user convenience and visual recognition, the system may query a database to determine what variants, if any, exist to potentially modify the root lexical. Each variant may represent a category having one or more options. Each root lexical may map to multiple medical classification codes via combination with different modifiers. These relationships may be precompiled, so that, rather than building the relationships each time a user selection is made, the query involves retrieving data reflecting those relationships, thereby shortening processing time and reducing the demand for system resources. Thus, upon receiving the user's root lexical selection, the system already may be aware of the variants necessary for further specificity.

The system then may generate visual maps based on the underlying mappings between the modifiers of each code set value. Visual depictions of multiple overlapping mappings may be generated at the same time, eliminating a need for a user to move back and forth between multiple displays.

Variants may be reflected as a series of parallel lines with the modifiers for each variant reflected as one or more nodes on each respective line, although other methods of arranging modifiers into groups and depicting those groups separately. Thus, in the example of FIG. 2, the user may have searched "diabetes" and selected the root lexical "Diabetes." This root lexical may include the variants of: "Diabetes mellitus type," "Diabetes mellitus complication," "Diabetes mellitus complication details," "Diabetes retinopathy severity," and "Diabetes mellitus macular edema." Each variant is depicted as its own line in the display, with each modifier shown as a circular node on the line. For example, the variant "Diabetes mellitus type" may include the following modifiers: "type 1," "type 2," "due to underlying condition," "drug or chemical induced," "other specified (including MODY)," and "gestational," each of which has its own node on the "Diabetes mellitus type" line.

The system also may generate curves or splines connecting all the nodes that yield fully-defined medical classification codes. As such, each spline represents both a combination and a classification code set value, e.g., an ICD-10 code. Each spline also may correspond to a fully specified interface terminology element, which may be considered a hyperprecoordinated term.

It is not necessary for a curve to pass through a node on every variant line in order to yield a fully-defined code. At one extreme, e.g., where a node is present without any connecting lines, that node itself may represent a fully-defined code, such as in the case of gestational diabetes on the Diabetes mellitus type variant line in FIG. 2. At the other extreme, a curve may pass through no more than one node on each and every variant line.

In order to distinguish differences between the code sets or release versions being compared, the system may generate visual indicators that highlight those differences. In one aspect, the system may apply a series of color-codings to reflect different changes. Thus, in one example, splines drawn in a first color such as gray may represent variant combinations that are unchanged from one version to another. Spines drawn in a second color such as blue may represent variant combinations that were added to a later version, while splines drawn in a third color such as orange may represent variant combinations that were removed from an earlier version, and splines drawn in a fourth color such as orange may represent variant combinations that were modified but not removed. Other visual indicators such as different line weights or line styles also may be used. In addition, the indicators may apply to individual nodes and/or variant lines as well. For example, a "macular edema" option on the bottom variant has been added to the visual map on the right in FIG. 2, and a visual indicator has been applied to the node to reflect that addition.

Staying with FIG. 2, the system also may display a listing of the changes as between displayed code sets, e.g., in a list underneath the visual maps. Each entry in the listing may include an indicator reflecting the type of change that was made from one code set to another, as well as the hyperprecoordinated term description and/or value and the classification code set description and/or value of the entry that was changed.

As can be seen from the representation of FIG. 2, certain root lexicals may yield a large number of curve mappings. In this "diabetes" example, there are over 600 distinct mappings, each of which would have needed to be checked individually in order to determine what changes, if any, were made from one code set to the next. With this system, the results are displayed visually to the user in a side-by-side, highlighted manner so that the changes are much more readily apparent to the reviewer. Additionally, the summary displayed proximate the visual maps indicates that 43 combinations were removed from the first code set and 79 combinations were added to the second code set. Thus, a reviewer may be able to focus his or her effort on these 122 changes rather than having to inspect all 600+ mappings. As a result, review and quality assurance (QA) time may be reduced drastically, which may permit faster deployment of the newer code set.

Figure 3:
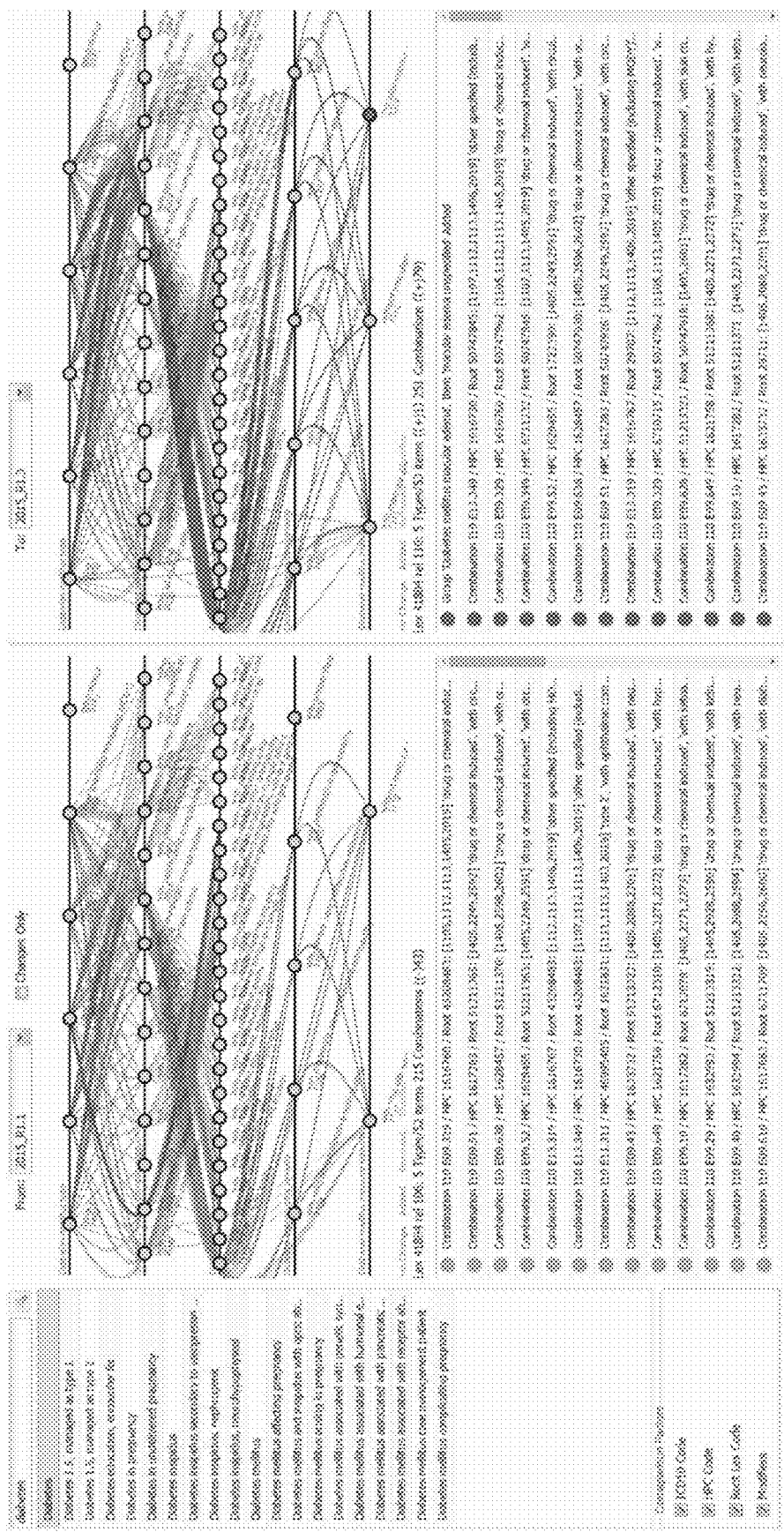
FIG. 3 is a screenshot of the interface of FIG. 2, with a single spline selected and highlighted.

Turning to FIG. 3, the system may be configured to receive a user selection of a single spline, which causes the spline to be highlighted in comparison to other splines. This highlighting also quickly and easily represents to the user the variants and their respective modifiers that formulate each pathway or code value. Thus, the user can determine instantly if the pathway is complete or if other variants should be considered. For example, in FIG. 3, the selected pathway does not include any mappings to the "Diabetic retinopathy severity" variant. If the user believes that this pathway should include one or more nodes in that variant, the depiction by the system instantly signals to the user that the mapping was incomplete. Additionally, if the selected curve is in the older code set and is not indicated as modified, then the user also knows that this deficiency has carried over to the newer version. Thus, the user can fix the mapping or signal to the system that additional modifications are necessary, ensuring greater accuracy and completeness of the newer version.

Figure 4:
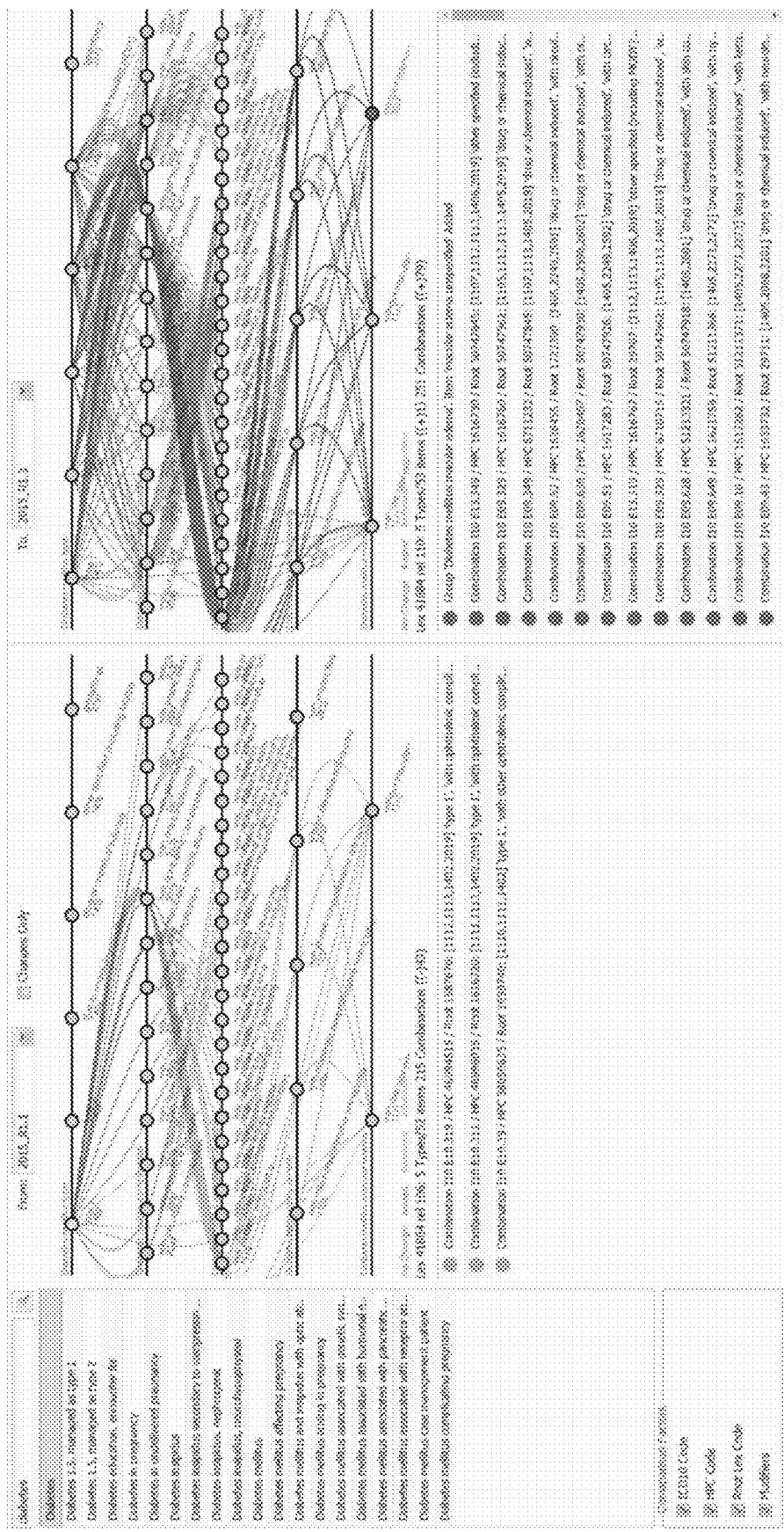
FIG. 4 is a screenshot of the interface of FIG. 2, with a single node/modifier on one visual map selected, with all splines passing through that node/requiring that modifier being retained on the display, and with all splines not passing through that node/requiring that modifier being hidden or otherwise suppressed.

The system also may receive user inputs in the form of modifier selections. Turning now to FIG. 4, this may be accomplished by selecting one or more nodes, which causes the system to remove all curves from the display that do not pass through the node. (Similarly, selecting a node that already has been selected removes that node from selection and may redraw or redisplay all curves that pass through other nodes on that variant level.) Similar to selecting a single spline as in FIG. 3, this option permits the user to review a subset of splines at a single time. Additionally, when the user selects a node, the system may update the summary of changes to reflect only those changes that relate to splines passing through those nodes. Thus, in the current example, the forty-three changes that occurred with respect to the code set in the first visual map are reduced to the three that pass through the "Type 1" node for the "Diabetes mellitus type" variant.

Figure 5:
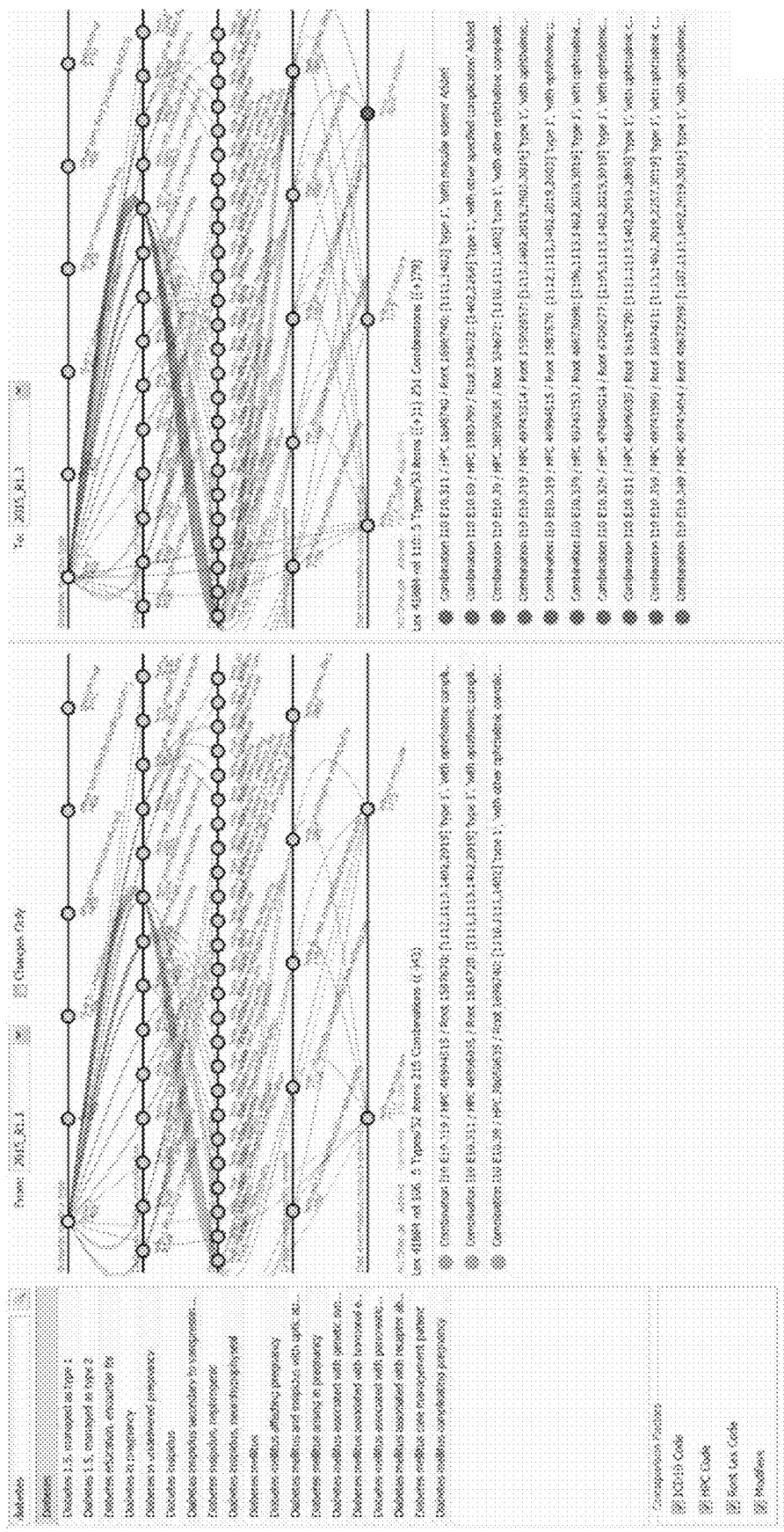
FIG. 5 is a screenshot of the interface of FIG. 4, with an identical node/modifier on each visual map selected and with the respective textual depictions being updated to present changes affecting only the splines passing through the selected node/modifier.

In order to assist in side-by-side comparisons of splines, a user may select the same node on each visual map, as depicted in FIG. 5. In addition to updating the listing of changes for each code set to reflect only changes involving the selected nodes, this feature permits the user to omit information that may be extraneous to the current analysis in order to focus and simplify that analysis.

Figure 6:
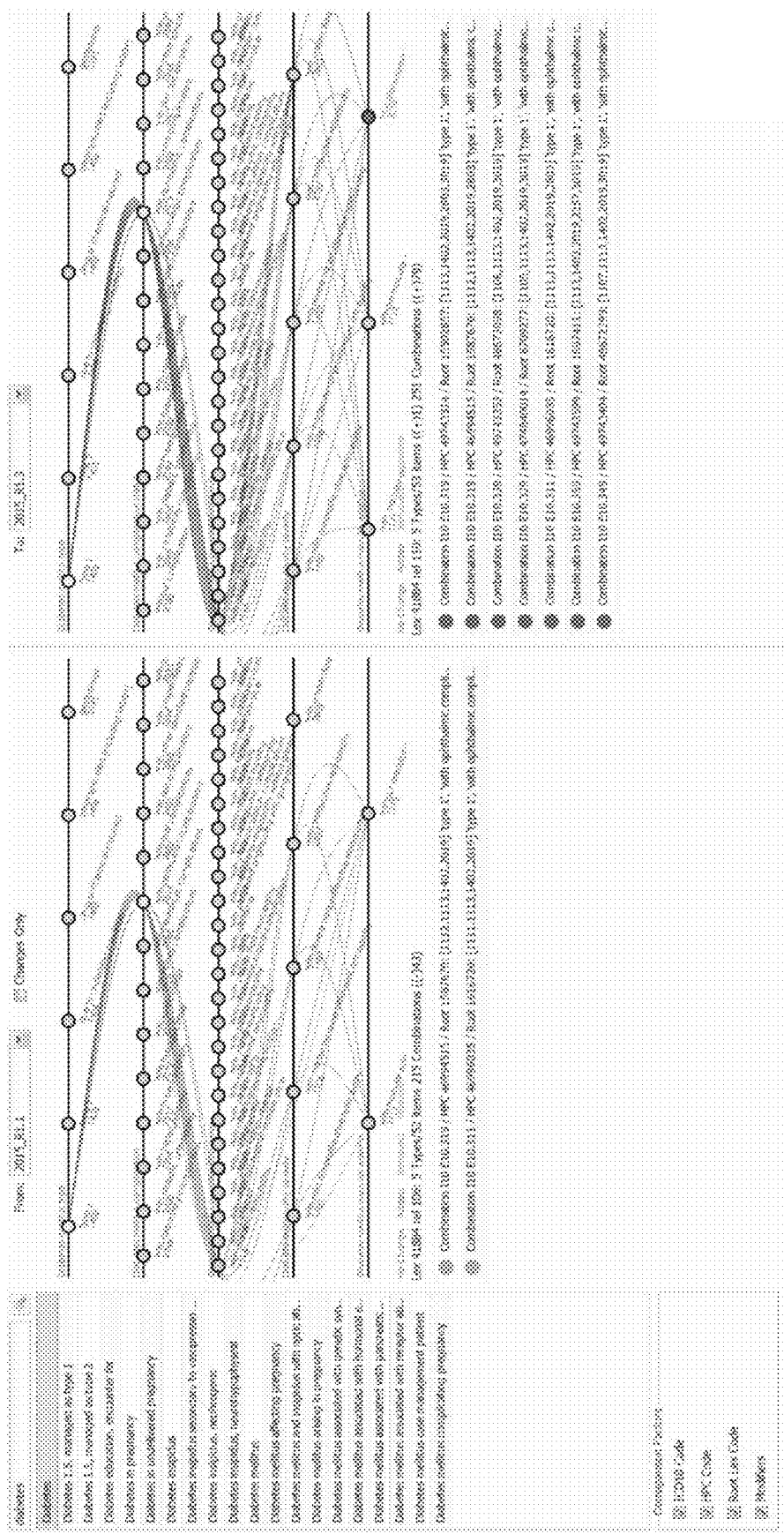
FIG. 6 is a screenshot of the interface of FIG. 5, with a plurality of identical nodes/modifiers for two variants on each visual map selected and with the respective textual depictions being updated to present changes affecting only the splines passing through the selected nodes/modifiers.
Figure 7:
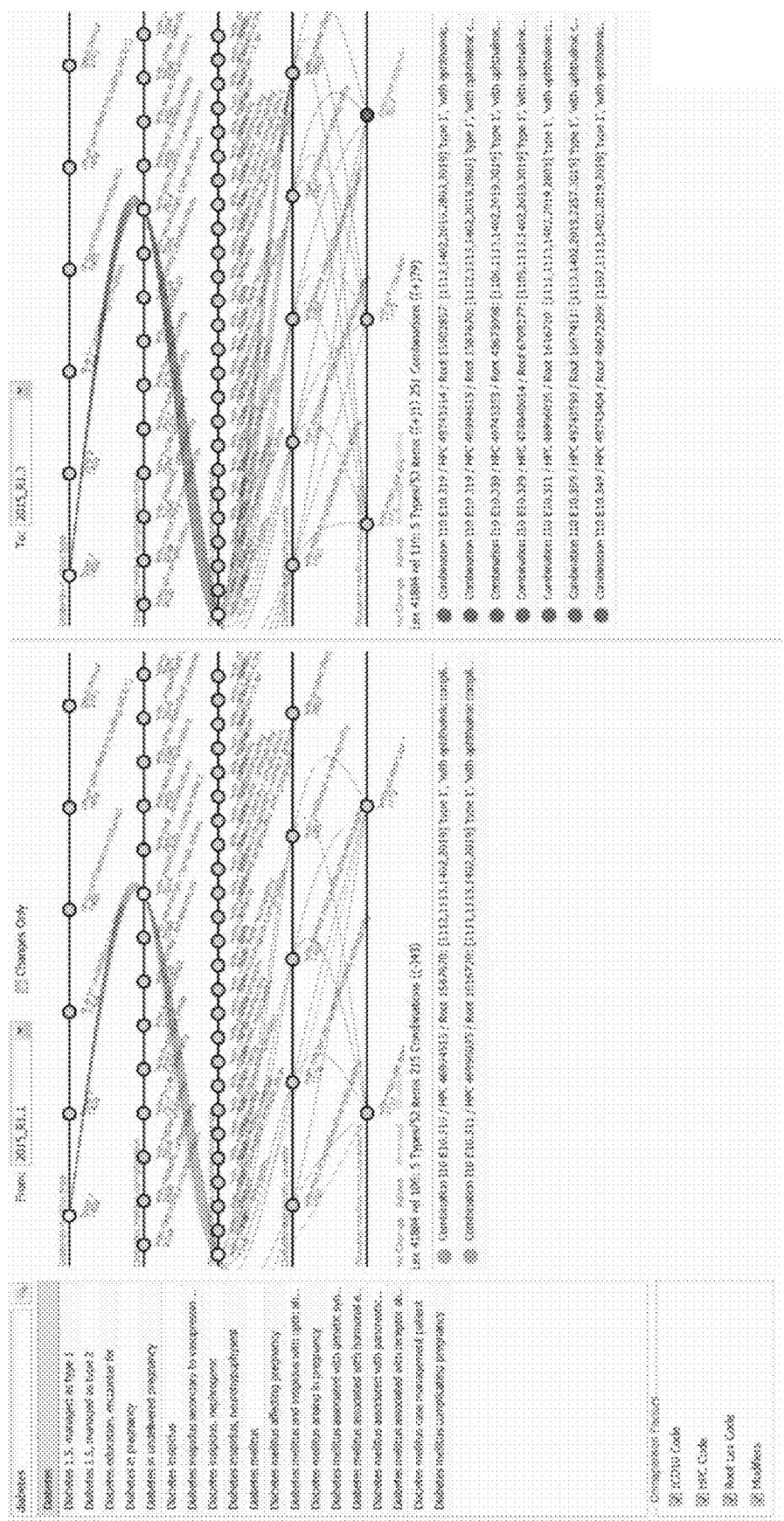
FIG. 7 is a screenshot of the interface of FIG. 6, with a plurality of identical nodes/modifiers for three variants on each visual map selected and with no changes to the respective textual depictions occurring as a result of the additional node specificity.
Figure 8:
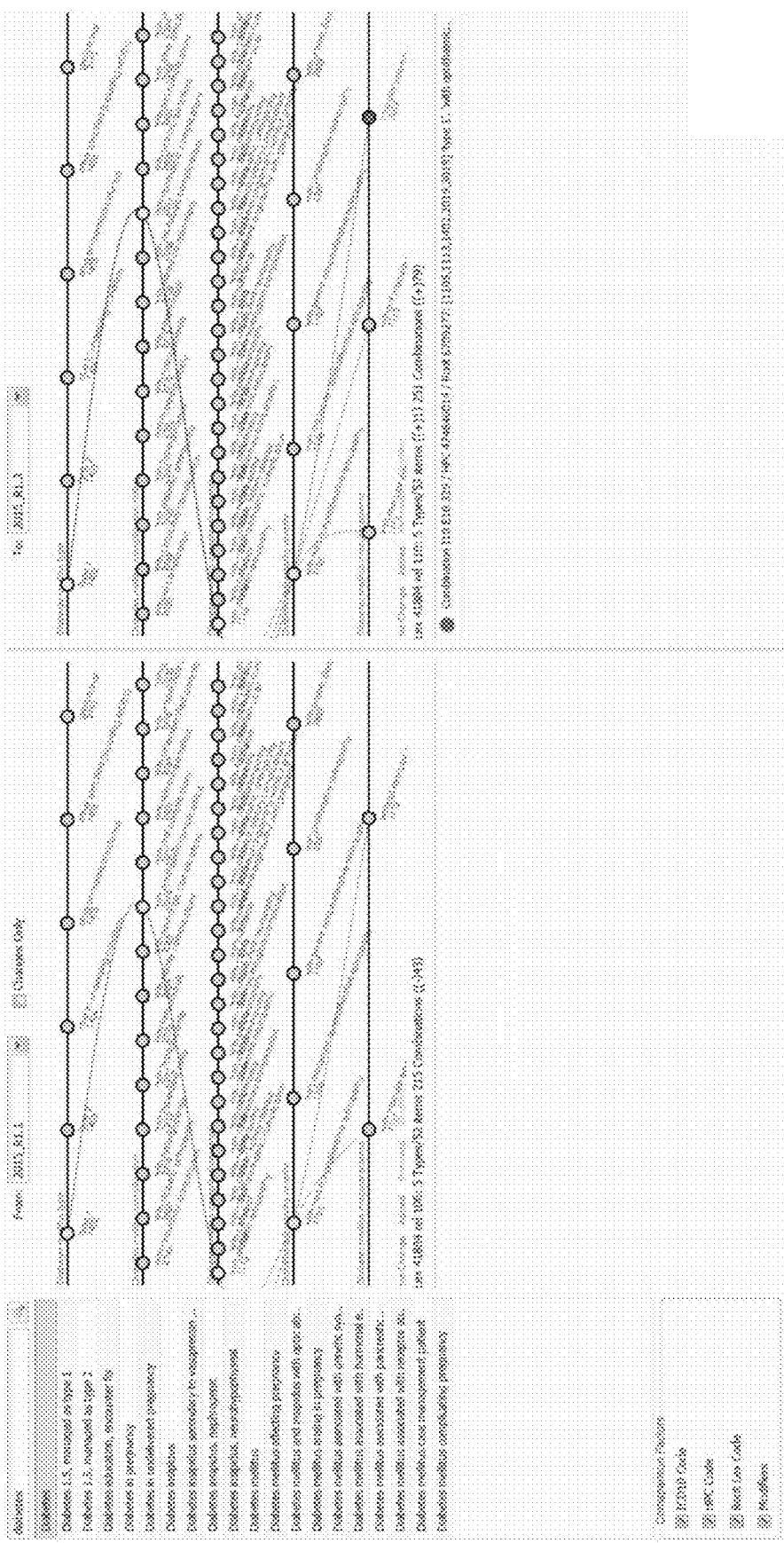
FIG. 8 is a screenshot of the interface of FIG. 7, with a plurality of identical nodes/modifiers for four variants on each visual map selected and with the respective textual depictions being updated to present changes affecting only the splines passing through the selected nodes/modifiers, if any.
Figure 9:
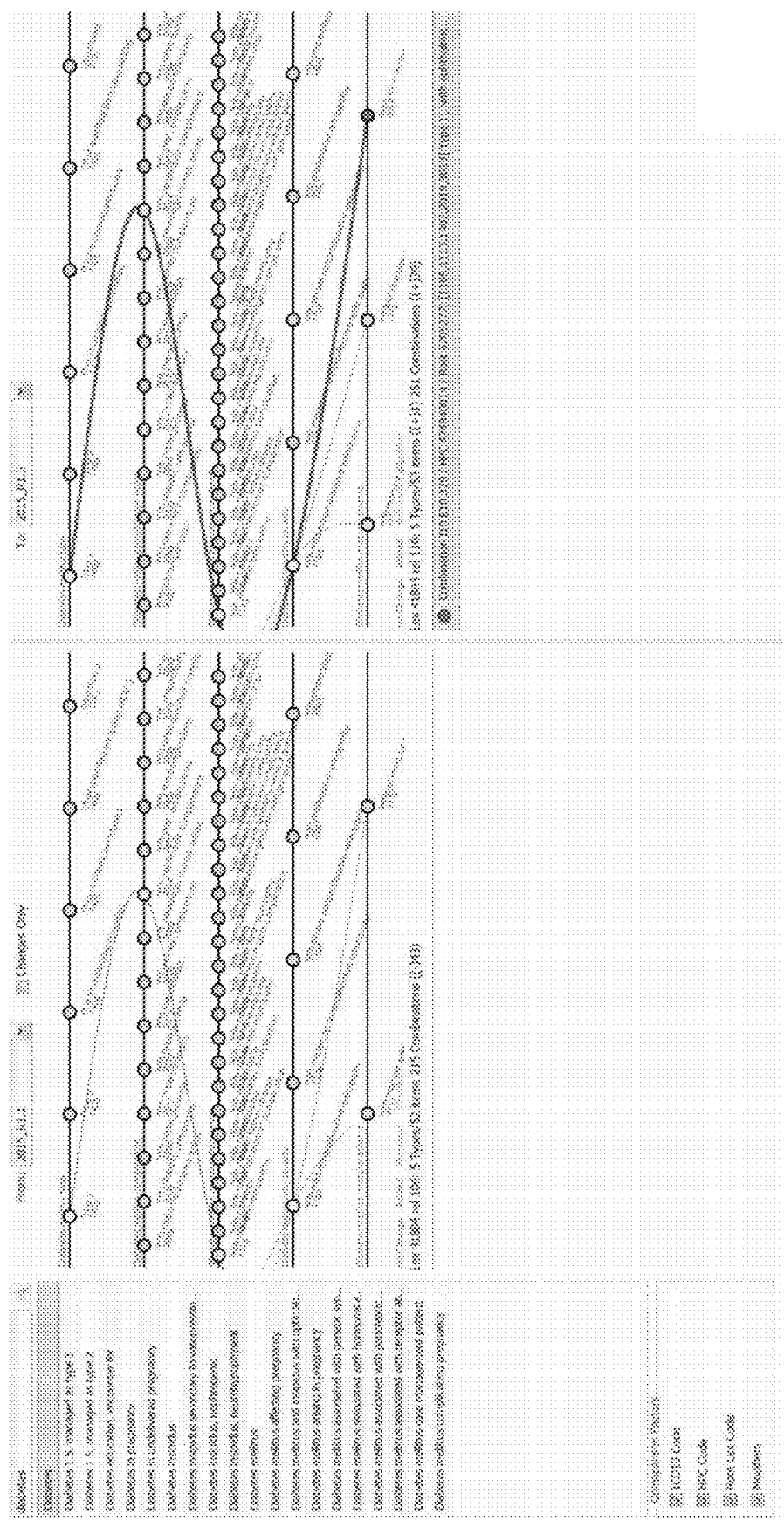
FIG. 9 is a screenshot of the interface of FIG. 8, with one spline within one of the visual displays selected and highlighted.

As seen in FIGS. 6-8, the system is configured to receive inputs for multiple nodes for each visual map in order to focus the analysis even further. Taken to one extreme, FIG. 9 depicts the visual maps of FIG. 8 with the only newly-added curve selected by the user and distinguished, e.g., highlighted, so that the user quickly and easily can determine its constituent variant modifiers. In these figures, the user has selected nodes from successive variants in the top-down order in which they are presented on the maps, but this ordering is not required. For example, the node selections in FIG. 7 could precede those of FIG. 6 with the same end result occurring. Additionally, in this example, the user has selected only a single node per variant. The system also may be configured to receive selections of multiple nodes per variant.

Figure 10:
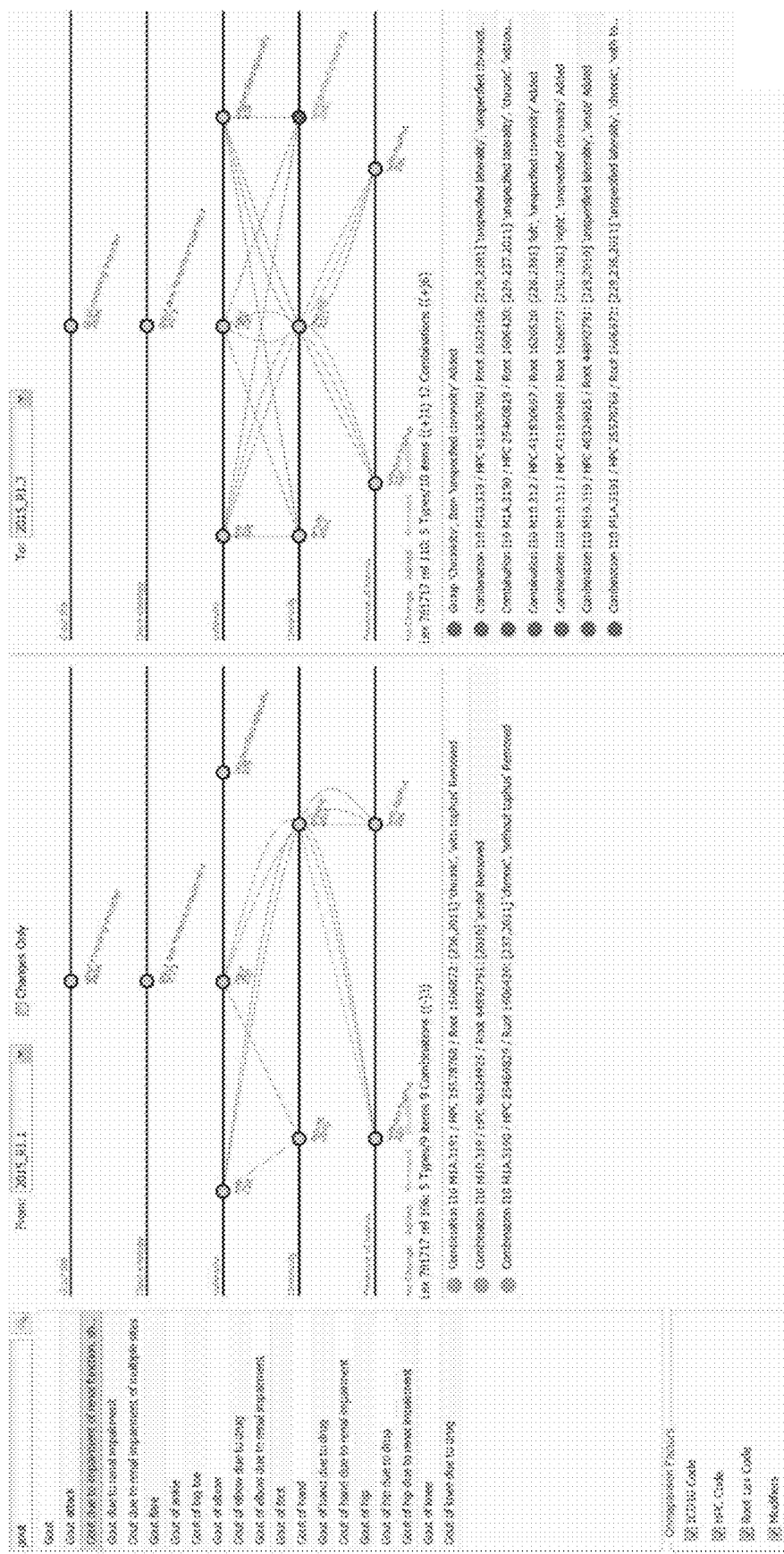
FIG. 10 is a screenshot of the interface of FIG. 1, displaying results in response to a different user query.

Turning now to FIG. 10, a second aspect of the system and method is depicted. In this aspect, as with the first aspect described above, the system may include a search function to receive a query from the user and to present the user with one or more root lexicals based on the user's input. Instead of a comparison tool to analyze mappings of one code set against another, FIG. 10 generates a single visual map based on the system's analysis of the user's root lexical selection. Thus, when the system receives a user selection, the system may cross-check that selection against a database of classification codes to determine what further variants are possible and populates the visual map with those variants and their respective modifiers.

Figure 11:
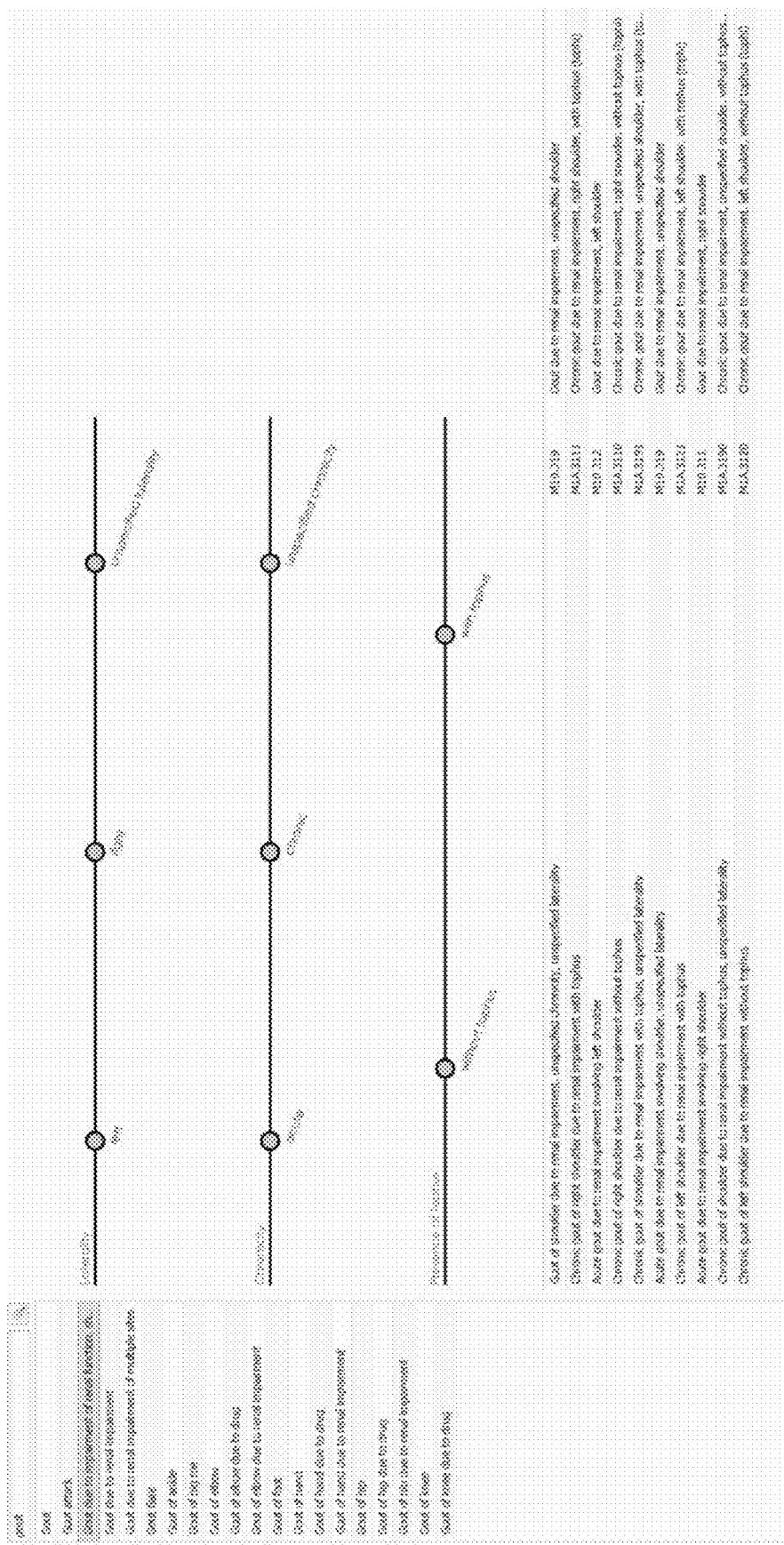
FIG. 11 is a screenshot of a second aspect of a user interface configured to receive a user query for a medical classification code, to return potential search results, and to generate and display visual maps to a plurality of interface terminology or medical classification code elements within a single version, revision, etc., of those codes.
Figure 12:
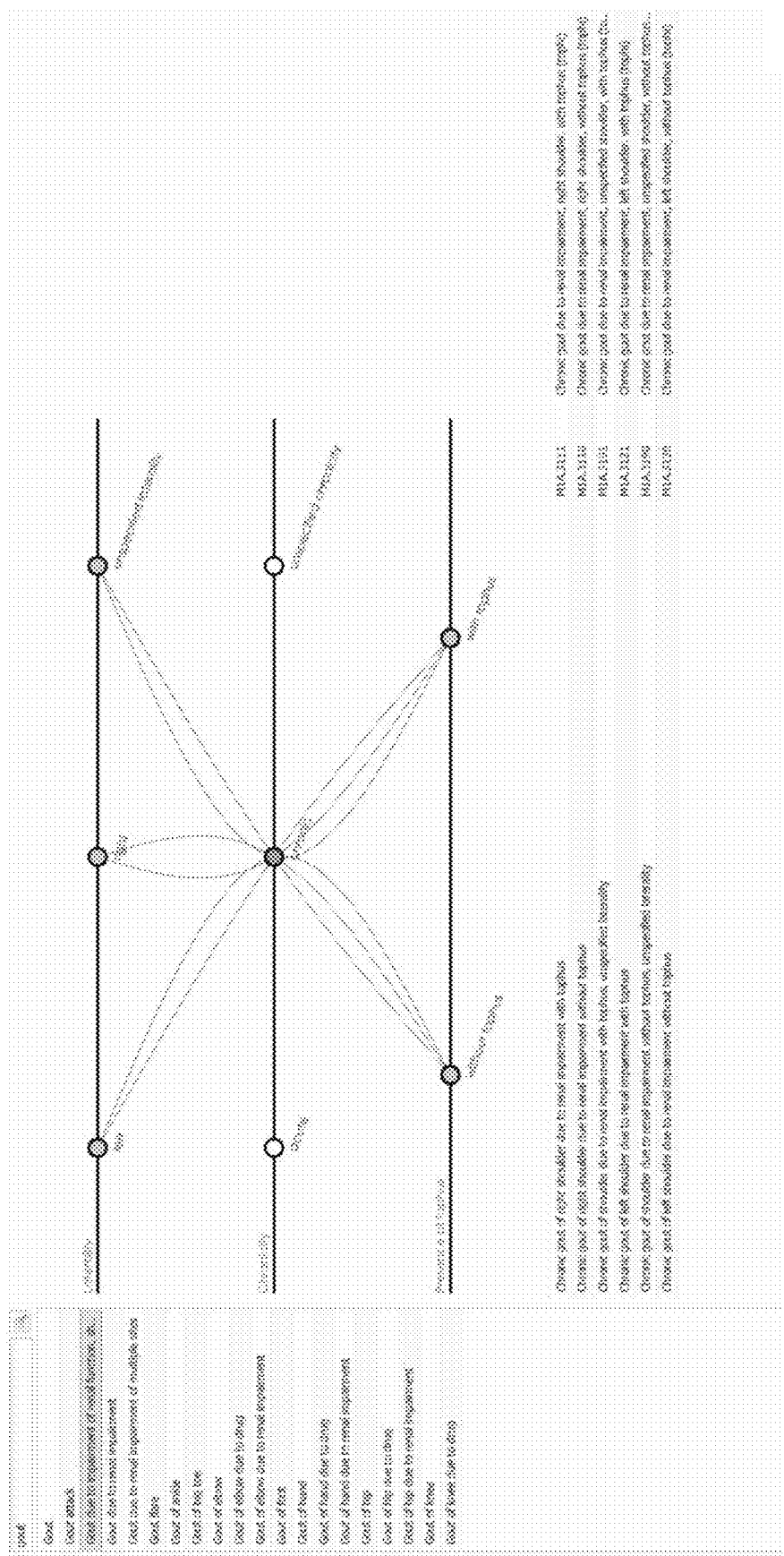
FIG. 12 is a screenshot of the interface of FIG. 11, displaying a visual map and textual depiction in response to a user selection from among search results returned in response to the user query.

As part of the same interface, the system also generates a listing of each classification code entry alongside the relevant classification code and a corresponding hyperprecoordinated interface terminology concept. In the example shown in FIG. 11, the root lexical selected by the user returns ten different classification codes. In other examples, such as in the diabetes example discussed above, the system may return dozens, if not hundreds, of potential results. Thus, should the user wish to narrow down the list of possible classification codes prior to making a selection, the user can select one or more nodes on the visual map, as at FIG. 12. Upon receiving a selection, the system modifies the visual map to generate reference splines for all classification codes that include mappings to interface terminologies including the selected node. Because the user's selection likely reduces the number of matching classification codes, the system also updates the classification code listing to remove or hide entries that do not include the selected node. In one example, the system updates the list by deleting or otherwise hiding non-matching entries. In another example, the system regenerates the list and only generates entries that match the selected criteria.

The system also may provide visual indicators for each node to give the user instant feedback as to the analytic state. For example, a first indicator such as a first node color or node shape may be applied to the node(s) selected by the user in order to alert the user to the fact that those nodes were selected. A second indicator such as a second node color or node shape may be applied to nodes that have possible links to the selected node based upon the user's root lexical choice. These nodes also may be the ones through which the generated curves in the visual map pass. A third indicator such as a third node color or node shape may exist for nodes that do not link to the selected node based upon the user's root lexical request. In one example, these nodes may appear unchanged as compared to before the user's node selection.

In another example, these third indicator nodes may alert a user to a discrepancy in the model. For example, if the user expects a certain medical classification code to correspond to an interface terminology code including a specific modifier, and if that modifier is color-coded to reflect no linking, the system may be suggesting to the user that the model is incorrect, and the user may submit a request to have the model reevaluated and/or corrected. This situation may exist for both this aspect and the side-by-side aspect described above, although if the third indicator node appears in the visual display for the earlier release, the system may alert the user to potential changes by permitting the user to compare that earlier release against the later, revised release.

Figure 13:
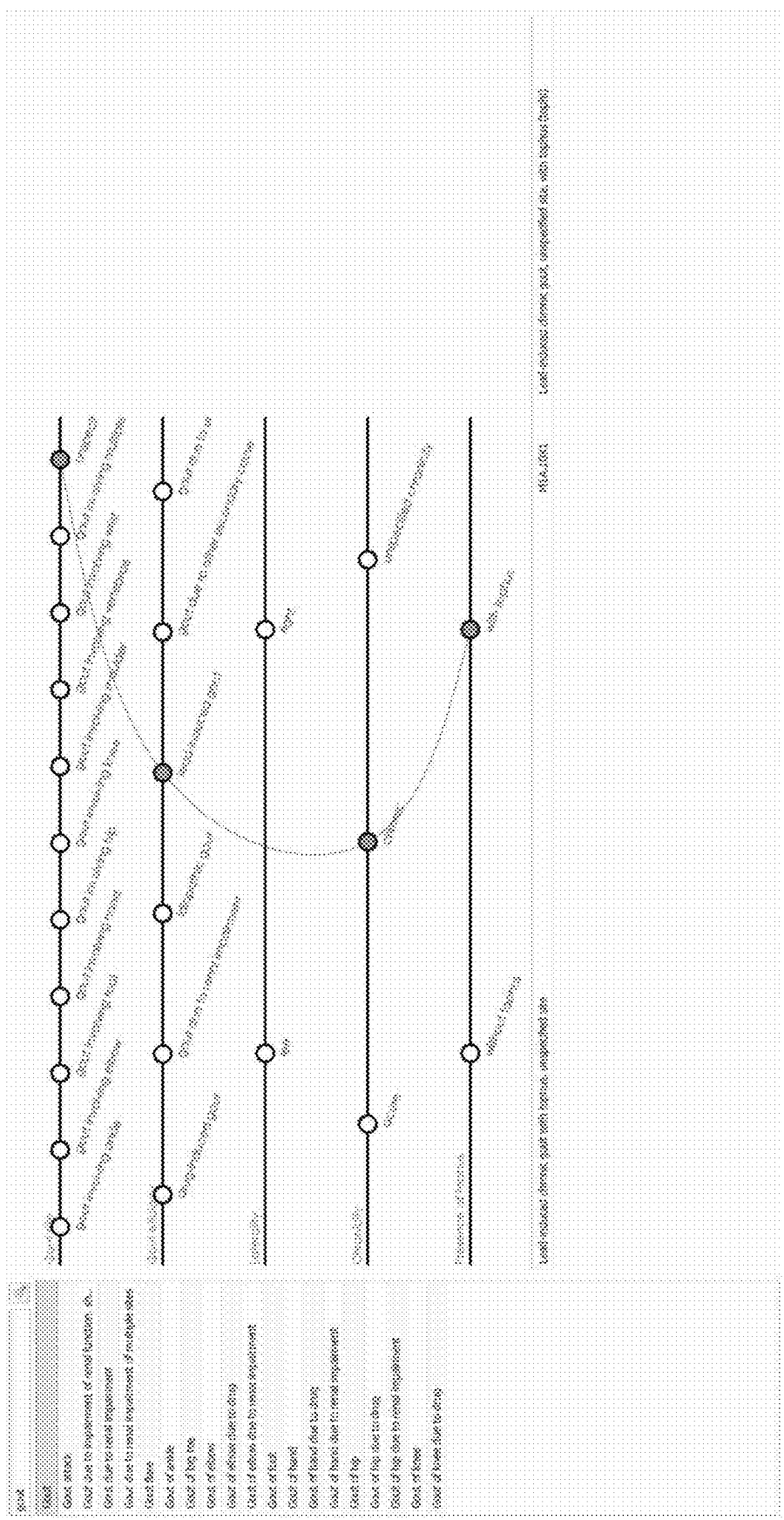
FIG. 13 is a screenshot of the interface of FIG. 11, displaying a different visual map and textual depiction from the map of FIG. 12 in response to a different user selection from among search results returned in response to the user query.

As with the multiple release comparison aspect described above, visual depiction in this second aspect gives the user a better idea of what modifier selections are necessary to get to a desired end result and which will have no effect. For example, for the root lexical selected by the user in FIG. 13, the user immediately may be able to discern that a selection for laterality has no effect on getting the user to his or her end selection, so the user does not need to waste time making a laterality selection. Alternatively, this absence of a modifier for the laterality variant may signal to the user that the mapping is incomplete. Thus, the current system and method achieve processing and analytical efficiencies over other analytical tools, such as those that feature a plurality of drop-down menus, with each menu relating to a variant and the options within that menu comprising the same or similar variant options as the ones displayed herein for each variant.

Textual depictions represent fully-defined pathways that have their own classification codes. Selection of a textual depiction then may eliminate all pathways in the visual map that do not correlate to the selection.

The system also presents a new way for a clinician to determine if a combination is modeled and, if not, to make a request for a new mapping. For example, a clinician may notice that there are curves passing through the left and right laterality nodes as well as curves that bypass those nodes but that there is no "unspecified laterality" node to accommodate those bypassers. Thus, the clinician may request that the classification code set be updated to include this variant option.

Figure 14:
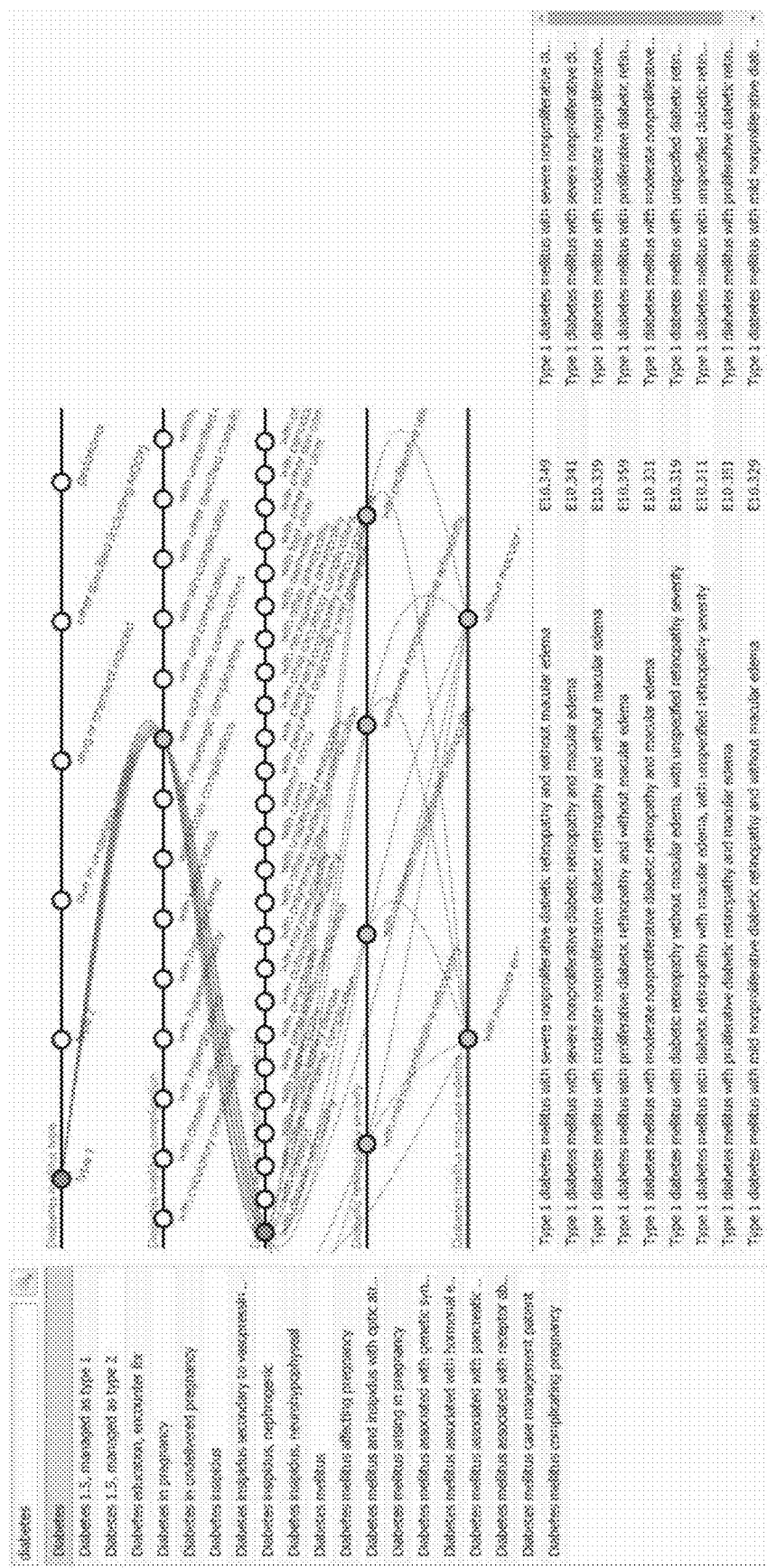
FIG. 14 is screenshot of the interface of FIG. 11, displaying a different visual map and different visual depiction in response to a different user query.

Turning now to FIG. 14, another example of the visual interface is shown. In this example, the user is presented with a visual map after selecting a root lexical, where the visual map includes multiple variants with widely varying numbers of options. Due to the visual representation of the mapping, the user quickly can tell that selecting a variant option from one of the variants that has a large number of possibilities can pare down the possible results more rapidly than selecting a variant option from a variant with only a few options. For example, there are twenty-five variant options on the third variant line, and selection of the first of these eliminates all mappings that pass through the other twenty-four options. In contrast, a user selection of one of the two variant options on the last line will reduce the number of returned mappings but to a considerably less degree. Thus, the current system again results in user efficiencies and faster analytics.

The system and method may be implemented on one or more computers in communication with one another. A first computer system may include one or more processors, memory, and storage including one or more databases storing the medical classification codes, the medical classification code descriptions, the interface terminology concepts and related descriptions/lexicals, the interface terminology identifiers/codes, and the relationships, i.e., the mappings between the various elements. A second computer system may be a user computer system that includes software for communicating with the first computer system, e.g., a web browser with a secure data connection. In another aspect, the first and second computer systems may be the same computer system.

The first computer system may receive the user's queries in one or more forms of data entry, e.g., keyboard entry, mouse clicks, stylus selections, touch screen selections, etc. In one aspect, each user query is transmitted from the second to the first computer system, where one or more forms of computational analysis are performed. Preferably, however, only search queries are transmitted back to the first computer system, where the first computer system analyzes each query, determines what interface terminology and medical classification code elements potentially relate to the searched term, packages those results, and then transmits that package back to the second computer system.

Search analysis may involve generating the mappings between various interface terminology elements and between those elements and the medical classification codes. Those mappings may be performed prior to the user queries, which may have one or more advantages. An initial mapping may mean that subsequent queries may rely on a lookup or similar operation to retrieve the necessary data, significantly increasing the speed with which those subsequent queries return results. Additionally, an initial mapping may mean that, once the mapping has been completed, its results are available to multiple users, again reducing overall system demand and thereby permitting greater system scalability.

The results may be packaged, e.g., in one or more XML files that include the search results and the relationships among elements in the search results. The packaged results, e.g., the XML files, also may include instructions for generating the visual maps and the splines disposed thereon, as well as instructions for generating the textual summary proximate the visual maps. Thus, in this aspect, the first and second systems may not need to be in communication after each user interaction. Instead, the second computer system may receive from the first computer system all of the information and instructions it needs to generate the visual maps and related textual summary and to modify those elements based on further user inputs.

The visual maps may be generated by one or more methods known for creating visual displays on a computer display. For example, the XML package of results may include instructions to generate each visual map as a scalable vector graphic (SVG). Those instructions may permit the second computer system to position and draw the visual map, including locating and identifying each variant, each node/modifier for each variant, and each spline. Subsequent user interactions may result in the computer system displaying or hiding one or more of those splines, in accordance with the logic rules described above.

The system may be integrated into or interfacing with electronic health record software such that selection of a classification code (or of an interface terminology hyperprecoordinated element mapping to a classification code) populates a selected field or entry within the record. As such, rapid, accurate entry or verification of electronic health records may be achieved.

In one aspect, EHR integration may occur in a similar manner, e.g., via one or more web services, as part of a vendor partner clinical solution working in conjunction with an EHR provider. For example, the clinical solution software may be configured to integrate a portal that receives user queries, communicates with the back-end first computer system, and returns the necessary information, e.g., in a packaged XML file. The clinical solution software also may be configured to generate the visual maps and textual depictions within that software's graphical user interface, e.g., by generating an SVG image or using other web technologies known to those skilled in the art.

From within that vendor partner clinical solution, an end user may be prompted to select one or many root lexical modifiers as appropriate, eventually visually narrowing down a selection to a hyperprecoordinated lexical term that maps to a very specific medical classification code. Upon selecting that term, the EHR interface may receive a data packet including the medical classification code, the related interface terminology hyperprecoordinated lexical term and/or code, and the mappings to the various interface terminology lexicals that result in the hyperprecoordinated term. The interface also may receive mappings between the hyperprecoordinated lexical and/or its constituent interface terminology lexicals and any other code sets, e.g., SNOMED codes, CPT codes, etc. The EHR then may insert at least the medical classification code into the relevant portion of a data file comprising a patient's medical record, e.g., in the portion of the file that records the patient's problem list, thereby updating the patient's medical record. The data file also may receive and store the interface terminology and/or other code set mappings, in the event that those values are needed for additional functionality, e.g., billing purposes.

While the foregoing written description of the invention enables one of ordinary skill to make and use what is considered presently to be the best mode thereof, those of ordinary skill will understand and appreciate the existence of variations, combinations, and equivalents of the specific exemplary embodiment and method herein. The invention should therefore not be limited by the above described embodiment and method, but by all embodiments and methods within the scope and spirit of the invention as claimed.

What is claimed is:

1. A method for medical classification code modeling, comprising:
   mapping, using a computer, a plurality of medical classification codes to a plurality of interface terminology elements;
   grouping the plurality of interface terminology elements into categories in a database, each category comprising a base element and one or more sub-elements, where each base element is less than a fully defined interface terminology concept, where each medical classification code maps to a respective combination of the base element with one or more modifiers selected from among one or more variants;
   receiving, using a computer, a search query from a user;
   comparing the search query against the database;
   determining, by the computer performing the receiving step, whether the search query matches one or more base elements;
   returning a list of base elements matching the search query;
   receiving a user selection of one of the base elements matching the search query; and
   generating an interactive visual map on a display screen of the one or more sub-elements underneath the user selection of the one of the base elements matching the search query;
   wherein the generating step includes arranging modifiers according to their respective variants and visually linking the one or more modifiers that represent each sub-element,
   the method further including receiving one or more selections of the one or more modifiers sufficient to generate a fully defined interface terminology concept.

2. The method of claim 1, further comprising:
   generating a textual depiction of each sub-element, wherein each textual depiction includes at least one of an interface terminology element summary, an interface terminology code, a medical classification code summary, and a medical classification code.

3. The method of claim 1, wherein the plurality of medical classification codes are ICD-10 codes.

4. The method of claim 1, further comprising generating a second visual map alongside the first visual map,
   wherein the first visual map is a first revision of a map of the one or more variants and the one or more modifiers per variant for the user selection of the one of the base elements matching the search query,
   wherein the second visual map is a second revision of a map of the one or more variants and the one or more modifiers per variant, and
   wherein visual inspection of the first and second visual maps indicates differences between the first and second revisions.

5. The method of claim 4, further comprising:
   generating a textual description proximate each visual map, wherein entries in the textual description include indicators of changes made to a respective visual map relative to the other visual map.

6. The method of claim 1, further comprising, for each received user selection of a modifier;
   removing from the visual map each sub-element that does not include the user-selected modifier.

7. The method of claim 6, further comprising:
   generating a textual depiction of each sub-element, wherein each textual depiction includes at least one of an interface terminology element summary, an interface terminology code, a medical classification code summary, and a medical classification code; and removing from the textual depiction each sub-element that does not include the user-selected modifier.

8. The method of claim 1, wherein the user selection of the one of the base elements matching the search query is an exact match to the search query.

9. The method of claim 1, wherein the user selection of the one of the base elements matching the search query is an approximate match to the search query.

10. The method of claim 1, further comprising:

importing a medical classification code corresponding to the fully defined interface terminology concept into an electronic health record.

11. A method for medical classification code modeling, comprising:

mapping, using a computer, a plurality of medical classification codes to a plurality of interface terminology elements;

grouping the plurality of interface terminology elements into categories in a database, each category comprising a base element and one or more sub-elements, where each base element is less than a fully defined interface terminology concept, where each medical classification code maps to a respective combination of the base element with one or more modifiers selected from among one or more variants;

receiving a search query from a user on a second computer;

comparing the search query against the database;

determining, by the computer, whether the search query matches one or more base elements; and returning, to the second computer, a data file including a list of base elements matching the search query;

wherein the data file includes data and instructions to generate an interactive visual map on a display screen of the one or more sub-elements underneath a user selection of one of the base elements matching the search query; and wherein the instructions include arranging modifiers in the interactive visual map according to their respective variants and visually linking the one or more modifiers that represent each sub-element, the method further including receiving one or more selections of the one or more modifiers sufficient to generate a fully defined interface terminology concept.

12. The method of claim 11, wherein the data file further includes data and instructions to generate a textual depiction of each sub-element, wherein each textual depiction includes at least one of an interface terminology element summary, an interface terminology code, a medical classification code summary, and a medical classification code.

13. The method of claim 11, wherein the plurality of medical classification codes are ICD-10 codes.

14. The method of claim 11, further comprising:

returning, to the second computer, a second data file including data and instructions to generate a second visual map alongside the first visual map, wherein the first visual map is a first revision of a map of the one or more variants and the one or more modifiers per variant for the user selection of the one of the base elements matching the search query, wherein the second visual map is a second revision of a map of the one or more variants and the one or more modifiers per variant, and wherein visual inspection of the first and second visual maps indicates differences between the first and second revisions.

15. The method of claim 14, wherein at least one of the first data file and the second data file includes instructions to generate a textual description proximate each visual map, wherein entries in the textual description include indicators of changes made to a respective visual map relative to the other visual map.

16. The method of claim 11, wherein the data file additionally includes instructions to, in response to each user selection of the one or more modifiers, remove from the visual map each sub-element that does not include the user-selected modifier.

17. The method of claim 16, wherein the data file additionally includes instructions to generate a textual depiction of each sub-element, wherein each textual depiction includes at least one of an interface terminology element summary, an interface terminology code, a medical classification code summary, and a medical classification code; and wherein the data file further includes instructions to remove from the textual depiction each sub-element that does not include the user-selected modifier.

18. The method of claim 11, wherein the search query match is an exact match.

19. The method of claim 11, wherein the search query match is an approximate match.

20. A system for medical classification code modeling, comprising:

a first computer system having a processor and at least one database, the first computer system in communication via a web service with one or more user computers, the at least one database including data representing a mapping of a plurality of medical classification codes to a plurality of interface terminology elements;

the at least one database grouping the plurality of interface terminology elements into categories, each category comprising a base element and one or more sub-elements, where each base element is less than a fully defined interface terminology concept, where each medical classification code maps to a respective combination of the base element with one or more modifiers selected from among one or more variants;

the first computer system configured to compare a search query received from a second computer against the database and to determine search query matches for one or more base elements;

the first computer system further configured to generate and to transmit to a second computer system a data file including a list of base elements matching the search query;

wherein the data file includes data and instructions to generate an interactive visual map on a display screen of the one or more sub-elements underneath a user selection of one of the base elements matching the search query; and wherein the instructions include arranging modifiers in the interactive visual map according to their respective variants and visually linking the one or more modifiers that represent each sub-element, the first computer system configured to receive one or more selections of the one or more modifiers sufficient to generate a fully defined interface terminology concept.

* * * * *